United States Patent [19]

Iyer

[11] 4,400,541

[45] Aug. 23, 1983

[54] PROCESS FOR PREPARING BIS-(DIPHENYLSULFONIOPHENYL)-SULFIDE BIS-CHLORIDE

[75] Inventor: Shankar S. Iyer, Hackettstown, N.J.

[73] Assignee: The Southland Corporation, Frankfurt am Main, Dallas, Tex.

[21] Appl. No.: 344,718

[22] Filed: Feb. 1, 1982

[51] Int. Cl.$^3$ ............................................. C07C 149/46
[52] U.S. Cl. ........................................ 568/56; 568/432
[58] Field of Search ............................. 568/56, 58, 74; 562/432

[56] References Cited

U.S. PATENT DOCUMENTS 2,807,648  9/1957  Pitt ........................................ 568/74
4,251,521  2/1981  Kathawala ............................ 568/74

*Primary Examiner*—Donald G. Daus
*Assistant Examiner*—M. C. Eakin
*Attorney, Agent, or Firm*—Cushman, Darby & Cushman

[57] ABSTRACT

Bis-(diphenylsulfoniophenyl)-sulfide-bis-chloride and related aryl sulfonium halides are produced in high yields and in high purity by reacting diphenyl disulfide (Ph—S—S—Ph) in benzene in the presence of aluminum chloride with gaseous chlorine according to the disclosed process.

5 Claims, No Drawings

PROCESS FOR PREPARING BIS-(DIPHENYLSULFONIOPHENYL)-SULFIDE BIS-CHLORIDE

BACKGROUND OF THE INVENTION

This invention relates broadly to a process of preparing arylsulfonium salts and more particularly to producing bis-(diphenylsulfoniophenyl)-sulfide bis-chloride (which for convenience will hereinafter be referred to as "bis") in higher yield and purity than has previously been possible.

Procedures for producing triaryl sulfonium salts are described in the relevant art. For example, U.S. Pat. No. 2,807,648 to Pitt describes reacting benzene or a halogenated benzene with aluminum chloride then reacting sulfur mono- or di-chloride then adding chlorine to produce a triaryl sulfonium chloride/aluminum trichloride complex.

This method produces mixtures of triarylsulfonium chlorides containing low to moderate proportions of "bis"—which is present in the reaction mixture which makes the isolation of the desired "bis" product difficult due to the physical and chemical similarity of the products. Alternative procedures using arylsulfides are undesirable due to the poor yields of the salt and relatively high expense.

The present invention overcomes the problems and disadvantages of the aforementioned methods by producing "bis" with improved yields and purity.

It is thus the primary object of the present invention to prepare mixtures of triaryl sulfonium chlorides with a higher content of "bis" than has been produced by other methods. Indeed, using the procedures of the invention purities in excess of 80% and approaching theoretical can be obtained. Using similar procedures other arylsulfonium halides can be produced economically and in good yields which arylsulfonium halides have not previously been readily available.

Additional objects and advantages of the invention will be set forth and will be apparent from the following detailed description of the invention.

DETAILED DESCRIPTION OF THE INVENTION

The compounds produced by the process of the present invention have the following general structure:

(Formula I)

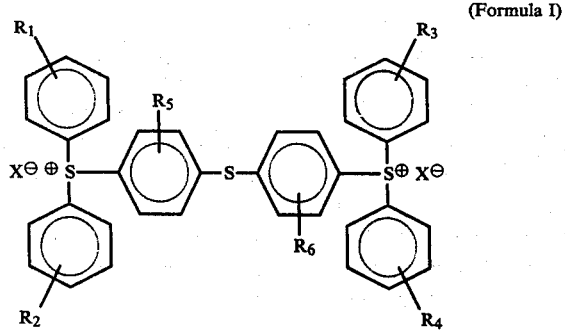

where $R_1$ through $R_6$ are independently hydrogen, halogen, carboxy, an ester, an aryl group or a phenyl group substituted by one or more halogen atoms, typically chlorine, or fused with the adjacent ring to form naphthalene. X is halogen, typically chlorine. These compounds are used to make starting materials for the manufacture of other salts, for example bis-(hexafluorophosphate), bis-(hexafluoroarsenate), bis-(hexafluoroantimonate) and bis-(tetrafluoroborate). These compounds have the primary utility as catalysts for curing ultraviolet activated coating compositions.

The process according to the invention comprises reacting a mixture of benzene, aluminum chloride and a diaryl disulfide with chlorine. The reaction proceeds essentially as follows assuming that the diaryl disulfide proceeds in 100% yield to "bis":

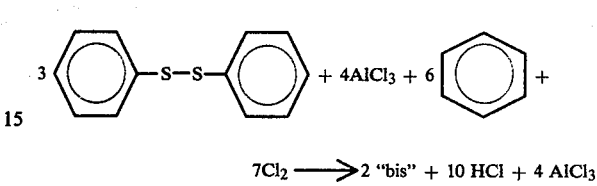

$7Cl_2 \longrightarrow 2$ "bis" $+ 10 HCl + 4 AlCl_3$

Ideally the temperature for the reaction is most suitable in the range of 0°–30° C. The purity of bis produced by the method of the invention is in excess of 80% and often approaches 100%. As the reaction proceeds HCl is produced which can be removed from the reaction vessel by known techniques.

When the reaction has gone to completion the mixture is drowned with water and ice and mixed. On standing the mixture separates into three layers. The top layer consists of unreacted benzene with soluble reactants and compounds produced by side reactions. The second layer consists of an aqueous solution of aluminum chloride with the bottom layer being an aqueous solution of the "bis" reaction product. The separation of the products from the reactants is performed by routine procedures for isolating the product.

The benzene used in the reaction is of commercial grade and in the preferred embodiment benzene is used in excess of the stochiometric amount as determined by the above reaction. The purpose of the excess benzene is two-fold. Initially it ensures that the reaction will proceed to completion and secondly the benzene serves as a slurrying agent for the reactants. The benzene also serves as a heat transfer agent and a solvent for any organic by-products formed. While benzene is the preferred solvent and slurrying agent other organic solvents can be used without deviating from the scope of the invention provided the organic solvent chosen does not interfere with the reaction. Other suitable solvents include aliphatic hydrocarbons which are optionally chlorinated, nitroalkanes and nitrobenzene. Solvents such as toluene, monochlorobenzene and others which take part in the reaction should not be used to make the desired bis-(diphenylsulfoniophenyl)-sulfide bischloride. Alternatively they can be used as reactants, as the case may be, to make the appropriately substituted aryl sulfonium halides. The selection of a suitable solvent or solvent system may be determined by a few experiments.

The essential reactant for the process is the diaryldisulfide. We have found that other organic sulfur compounds, while reactive, are not preferred in that they are not capable of forming the desired product in a yield as high as diphenyl disulfide. For example, diphenyl (mono) sulfide produces relatively low yields of "bis" as compared to the disulfide. The purity of this raw material is also lower.

While the preferred embodiment of the process uses diphenyl disulfide, other substituted diaryldisulfides may be used to produce the corresponding salts. Among other substituted diphenyldisulfides which can be used and still produce equally high yields of the desired product are those substituted with one or more phenyl groups. Likewise the substituents may be on one or both of the phenyl groups and still retain their capability of undergoing conversion to the respective disulfide. By diphenyldisulfide compounds of the formula Ph·S·S·Ph are intended.

Catalysts for the reaction are categorized as Lewis acids. While aluminum chloride is the most desirable catalyst it is possible to use other Lewis acids, including for example ferric chloride, zinc chloride, stannic chloride, aluminum bromide, boron trifluoride, hydrofluoric acid and phosphoric acid. It is preferred, however, to use a chlorine-containing acid. The quantity of the Lewis acid used is preferably at least a stochiometric amount as it is considered to have an influence on product yield. Two moles of aluminum chloride will be consumed during the reaction whereas if a mono or dichloro acid is used the molar amount must be adjusted accordingly. A moderate excess beyond the stochiometric amount may be used for increasing the rate of reaction and the extent of completion, however a large excess is not particularly desirable due to the added expense compared with the actual benefit obtained.

The preferred halogen used is chlorine, however other halogens may be substituted as desired. The amount of halogen used should be limited to an amount that is required to complete the reaction. The actual amount consumed will vary and may be determined by usage. Factors which will determine the amount of chlorine used include: temperature, rate of introduction and pressure of the reaction vessel as well as its physical dimensions and operating characteristics thereof.

Although chlorine is relatively inexpensive, a large excess is not recommended as little or no benefit in the reaction rate is observed. Likewise with excess chlorine efforts to recover the excess chlorine become burdensome as well as possible destruction of the desired end product. It is noted that the process is not limited to chlorine but other halogens, typically bromine, may be used as desired to produce the specified sulfide. When it is desired to make compounds of Formula I where X is other than chlorine then it is preferred that a corresponding catalyst be used having the same halogen to prevent possibility of undesirable mixtures.

The process of the present invention will be further illustrated in the following non-limiting Example, which is in accordance with the present invention, and Comparative Example in the manner of U.S. Pat. No. 2,807,648 to Pitt. Unless otherwise indicated all parts and percentages are by weight.

EXAMPLE

Benzene (230 g) and diphenyl disulfide (54.2 g; 0.25 mole) were introduced into a flask (500 ml) fitted with a stirrer. The mixture was stirred and a clear yellow solution was obtained. The solution was cooled to about 10° C. and anhydrous aluminum chloride (80 g) was added.

Chlorine gas was sparged into the flask while maintaining the reaction temperature at 10°–18° C. Approximately 95 g of chlorine were introduced during the course of the reaction. The mixture was poured into ice (300 g) and stirred until the aluminum chloride had completely dissolved. The solution was then heated to 60° C. and allowed to settle for 30 minutes. The lower product layer was drained then extracted with a solution of concentrated sulfuric acid (14 g) in water (140 g) at 60° C. The mixture was again allowed to settle and the lower product layer separated. The product layer was then extracted with 50% sodium hydroxide solution (20 g) in water (60 ml) at 60° C. On settling the solution yielded 160 grams of product which contained 76 grams (0.12 mole) of the desired product, 4,4-bis-(diphenylsulfoniophenyl)-sulfide bis-chloride, 42.29% of water and 0.22% of inorganic salts. By difference therefore the yield of organics was 92 grams. The purity was 82.6%.

Yield Calculation: 0.25 moles of diphenyl disulfide contains 0.5 atoms of sulfur. Since the "bis" contains 3 atoms of sulfur per mole the theoretical yield is 0.5÷3 moles % yield=(0.12/0.5÷3)×100%=72% of theory

COMPARATIVE EXAMPLE

This example is in the manner of Example 1 of U.S. Pat. No. 2,807,648. Benzene (230 g) and anhydrous aluminum chloride (80 g) were charged into a flask (500 ml) fitted with a stirrer. The contents of the flask were stirred and cooled to 10° C., then sulfur monochloride (50 g, 0.27 moles) was added to the reactants with stirring while maintaining the temperature of the reaction at 13°–16° C. The reaction mixture was agitated for one hour at 13°–16° C. then dry chlorine was sparged into the flask at 13°–16° C. About 100 g of chlorine was required to complete the chlorination reaction.

After completion the reaction mixture gas poured onto ice (300 g) and stirred until the aluminum chloride was completely dissolved. The solution was heated to 60° C. and settled, then the product layer was drained. The product layer was extracted with an aqueous sulfuric acid solution (25 g of $H_2SO_4$ in 300 g water), the mixture was settled and the lower product layer separated. The product layer was again extracted, this time with an aqueous solution of sodium hydroxide (20 g of 50% NaOH in 96 ml water).

The product was separated to yield 216 g of product which, by assay, was determined to contain 60.5 grams (0.097 moles) of 4,4'-Bis-(diphenyl sulfonio phenyl) sulfide bis-chloride, and 48.39 of water and 0.13% of inorganic salts. By difference therefore the yield of organics was 111.2 g. The purity was 54.4%.

Yield Calculation: 0.37 moles of sulfur monochloride contains 0.74 atoms of sulfur. Since the "bis" contains 3 atoms sulfur per mole of bis the theoretical yield was 39.3%.

It will be apparent to those skilled in the art that various modifications and variations can be made in the process of the present invention without departing from the scope or spirit of the invention.

What is claimed is:

1. A process of preparing an aryl sulfonium halide of the formula:

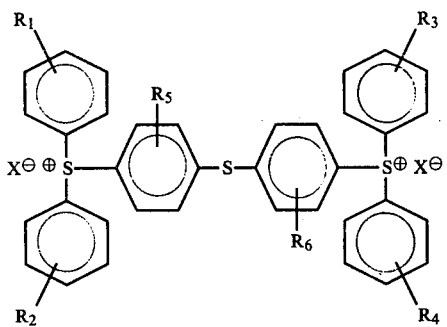
(Formula I)

wherein X is chlorine, bromine or fluorine, and $R_1$, $R_2$, $R_3$, $R_4$, $R_5$ and $R_6$ are independently hydrogen, halogen, a carboxy, a phenyl or a halo-substituted phenyl, said process comprising the sequential steps of:

(1) reacting a diaryl disulfide of the formula: Aryl-S-S-Aryl and aluminum chloride with a stoichiometric excess of benzene in a non-reactive organic solvent to form a reaction mixture;

(2) bubbling a gaseous halogen X, as defined above, into the reaction mixture; and (3) removing the aryl sulfonium halide product of Formula I thus produced.

2. A process of producing 4,4'-Bis-(diphenyl sulfoniophenyl)sulfide bis-chloride comprising reacting diphenyl disulfide with at least a stoichiometric amount of aluminum chloride and a stoichiometric excess of benzene optionally in an inert aromatic organic solvent to form a reaction mixture, then adding gaseous chlorine to the reaction mixture to produce 4,4'-Bis-(diphenyl sulfoniophenyl)sulfide bis-chloride.

3. The process of claim 1 or 2 wherein the reaction is conducted at a temperature in the range of about 0° to about 30° C.

4. The process of claim 3 wherein the reaction is conducted at a temperature of about 12° to about 15° C.

5. The process of claim 2 wherein benzene is the organic solvent.

* * * * *